United States Patent
Ohlander et al.

(10) Patent No.: US 10,349,162 B2
(45) Date of Patent: Jul. 9, 2019

(54) BATTERY COMPARTMENT SOLUTION FOR A HEARING PROTECTION DEVICE

(71) Applicant: Honeywell International Inc., Morris Plains, NJ (US)

(72) Inventors: Lisa Ohlander, Domsten (SE); May Wilson, Wokingham (GB); Alex Xu, Shanghai (CN)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/840,057

(22) Filed: Dec. 13, 2017

(65) Prior Publication Data

US 2018/0184194 A1    Jun. 28, 2018

(30) Foreign Application Priority Data

Dec. 22, 2016    (EP) ..................... 16206229

(51) Int. Cl.
*A61F 11/06* (2006.01)
*H04R 1/10* (2006.01)
(Continued)

(52) U.S. Cl.
CPC ............ *H04R 1/1083* (2013.01); *A61F 11/14* (2013.01); *H04R 1/1008* (2013.01);
(Continued)

(58) Field of Classification Search
CPC ...... H04R 1/1083; H04R 1/1041; H04R 1/10; H04R 1/1058; H04R 1/1066;
(Continued)

(56) References Cited

U.S. PATENT DOCUMENTS 7,097,746 B1 * 8/2006 Tzviskos ............ H01R 9/0518
204/196.23
2008/0069391 A1 * 3/2008 Steyn .................... H04R 1/1025
381/371
(Continued)

FOREIGN PATENT DOCUMENTS

WO        9912385 A1    3/1999
WO     2016126476 A1    8/2016
WO  WO-2016126476 A1 *  8/2016 .............. A61F 11/14

OTHER PUBLICATIONS

Community Design Registration No. 003534205-0001, Notice of Registration of Community Design, dated Dec. 22, 2016, 5 pages.
(Continued)

*Primary Examiner* — Leshui Zhang
(74) *Attorney, Agent, or Firm* — Wick Phillips Gould & Martin, LLP

(57) ABSTRACT

Embodiments relate generally to hearing protection devices comprising a battery compartment with a removable cover. Generally, the removable cover has two configurations: an unlocked configuration and a locked configuration. Typically, the removable cover may include a key and be configured to assist in one-handed removable by a gloved user (e.g. while the hearing protection device is being worn). So, for example, upon unlocking, the key might be configured to pop out automatically to allow the user to grasp the key and remove the removable cover.

20 Claims, 10 Drawing Sheets

(51) Int. Cl.
    *A61F 11/14*     (2006.01)
    *H04R 1/02*     (2006.01)

(52) U.S. Cl.
    CPC ........... *H04R 1/1041* (2013.01); *H04R 1/023* (2013.01); *H04R 1/1058* (2013.01)

(58) Field of Classification Search
    CPC ...... H04R 1/1091; H04R 1/1008; H04R 1/02; A61F 11/14; A61F 2011/145; A61F 2011/008; E05B 47/00–0696
    USPC ... 381/26, 309, 312–331, 71.6, 71, 73.1, 74, 381/FOR. 137, 72; 455/573, 572, 574, 455/575.1, 343.1, 343.2–343.6; 394/413, 394/433.08; 700/94
    See application file for complete search history.

(56) References Cited

U.S. PATENT DOCUMENTS

2014/0259287 A1\* 9/2014 Waters .................... A61F 11/14
    2/209
2015/0117660 A1     4/2015 Fletcher et al.

OTHER PUBLICATIONS

European Patent Application No. 16206229.3, Extended European Search Report, dated Jun. 6, 2017, 7 pages.
United States Design U.S. Appl. No. 29/608,508, filed Jun. 22, 2016, 19 pages.
China Design Patent Application No. 201730259110.4, filed Jun. 22, 2017, 40 pages.

\* cited by examiner

BATTERY COMPARTMENT SOLUTION FOR A HEARING PROTECTION DEVICE

CROSS-REFERENCE TO RELATED APPLICATIONS

The present application claims priority to Europe Patent Application No. 16206229.3 filed Dec. 22, 2016 by Lisa Ohlander et al. and entitled "BATTERY COMPARTMENT SOLUTION FOR A HEARING PROTECTION DEVICE" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments generally relate to hearing protection devices comprising a battery compartment with a removable cover, for example mounted in an ear cup of the hearing protection device.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
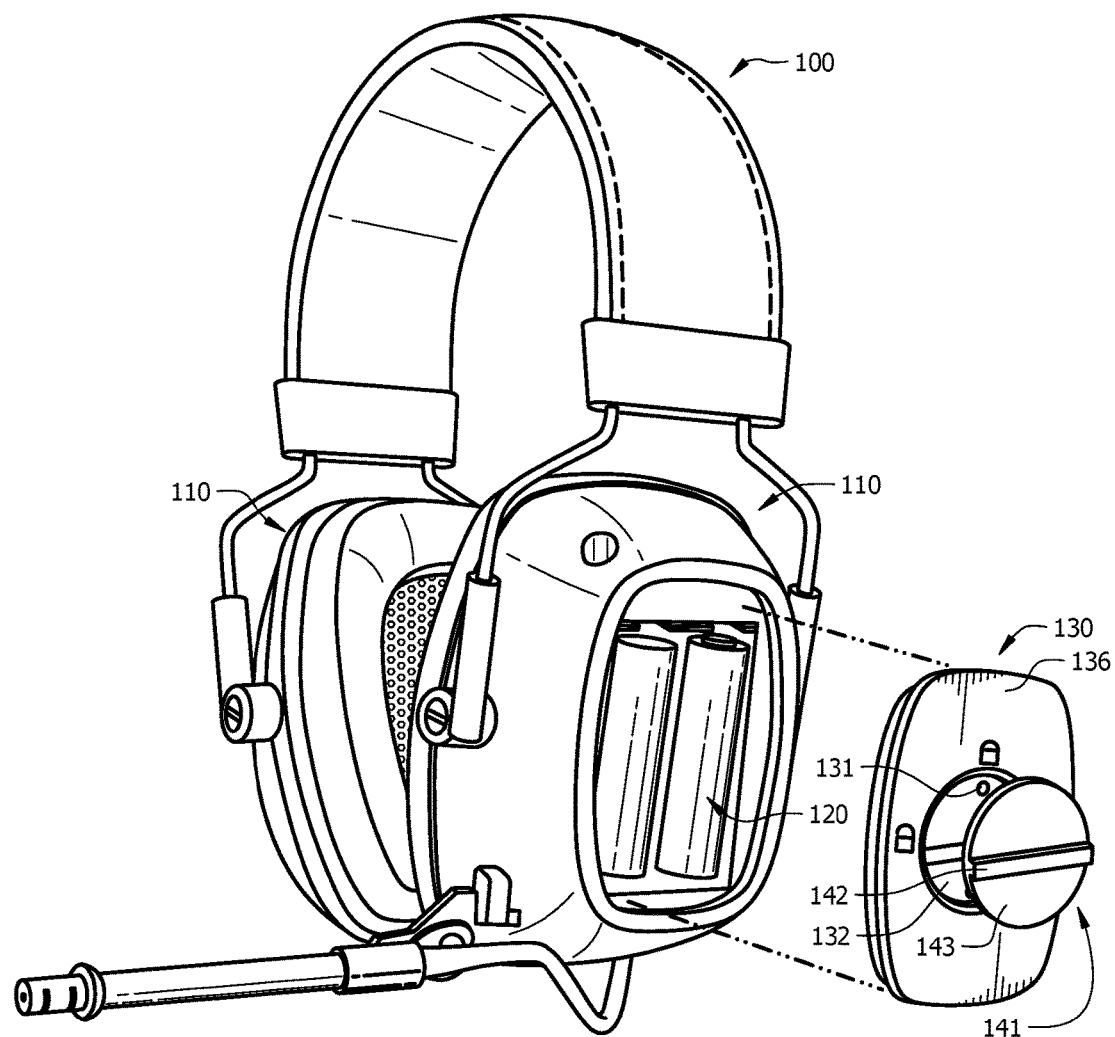
FIG. 1 illustrates a perspective view of an exemplary embodiment of a hearing protection device comprising an ear cup which further comprises a battery compartment, a removable cover, and a key.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The embodiments of this disclosure typically relate to hearing protection devices comprising a battery compartment, and, more specifically, relate to battery compartments comprising a key configured to ease the removal process of the removable cover (e.g. to replace batteries). Conventionally, hearing protection devices may comprise a battery compartment having a removable cover which requires the user to pull on a U-shaped cantilever snap-fit located on one end of the removable cover and pull out the removable cover once the U-shaped cantilever snap-fit is loose enough. Typically, the U-shaped cantilever snap-fit on the removable cover is small and may require the use of a tool to ease the difficulty of removing the removable cover via the user's hands. Thus, when users of hearing protection devices within industry need to remove the removable cover (e.g. to replace the batteries), the users may have to leave their area of work, remove their personal protective equipment (e.g. hearing protection device, gloves, etc.), detach the removable cover from the battery compartment, replace the batteries, attach the removable cover to the battery compartment, and replace (e.g. don) their personal protective equipment (e.g. hearing protection device, gloves, etc.) before going back to their area of work. In some instances, the user may attempt to remove the removable cover in his/her designated area of work. In this case, the user may face a safety hazard (e.g. potential hearing damage) from not wearing his/her hearing protection device within a loud working environment (since typically they would have to remove their hearing protection device to replace the batteries). Additionally, the user may face a safety hazard from having to remove his/her gloves to adequately grasp the U-shaped cantilever snap-fit on the removable cover (since conventional cover removal is extremely difficult while wearing gloves). Also, the user may risk misplacing or losing the removable cover, for example while trying to replace the batteries. The Applicants have constructed a battery compartment with an improved removable cover (e.g. comprising a key) to allow the user to more easily and quickly attach and detach the removable cover. In some embodiments, the device may also comprise a linking element which connects the removable cover to the battery compartment so the user may not potentially lose the removable cover. Also, the removable cover with the key may be configured for use with one hand (for example, even when wearing gloves) and may allow the user to replace batteries with greater ease (for example, while still wearing the hearing protection device). This can be especially important for users with hearing protection devices which have high power consumption (e.g. requiring replacement of batteries approximately 1-2 times per week). Additionally, the Applicants have constructed a device which may be used both indoors and outdoors, withstand water from entering into the battery compartment, and prevent air from entering into the ear cup (which might otherwise negatively impact the noise reduction rating (NRR)/hearing protection of the hearing protection device). Thus, disclosed embodiments may address one or more of such issues with the conventional removable cover located on a battery compartment to increase the ease of removal for the user while also maintaining the sound attenuating properties of the hearing protection device.

Disclosed embodiments relate to hearing protection devices (such as an ear cup of protective ear muffs) comprising a battery compartment having a removable cover. In this disclosure, the removable cover typically comprises a key and a main body panel portion. The key may typically be configured to allow the user to detach and attach the removable cover to the battery compartment. In some embodiments, the removable cover may comprise a through-hole and a recessed portion. Generally, the through-hole may be configured to fit (e.g. correspond with) the key (e.g. to allow the key to slide back and forth through the through-hole and rotate within the through-hole), and the recessed portion (typically located on the exterior of the main body panel portion) may be configured to snugly fit the external portion of the key (e.g. the grip surface). Additionally, the removable cover may comprise a sealing element around the outer circumference to allow the removable cover to seal with the battery compartment. Also, in some embodiments, there may be a second sealing element located between the key (e.g. the grip surface) and the removable cover. Typically, the sealing elements may prevent water from entering into the hearing protection device and may have an International Protection (IP) 54 rating designated for devices that prevent water from spraying into the device from any direction. In some embodiments, there may be a bias element located between the removable cover and the key (more specifically, within the recessed portion of the removable cover). The bias element may be configured to allow the key to be biased/pushed outward away from the removable cover. Additionally, in disclosed embodiments, the battery compartment may comprise a lock-fit aperture configured to correspond with the distal end of the key (to allow the removable cover to lock and unlock from the battery compartment). Thus, exemplary embodiments typically comprise: a battery compartment (with a lock-fit aperture) and a removable cover which may further comprise a key, a main body panel portion, a through-hole, a recessed portion, and a bias element. These and other additional elements will be discussed in more detail in the following paragraphs.

In this disclosure, the key typically may comprise a raised grip, a longitudinal member, and a pin. Additionally, in some embodiments, the key may comprise a circular back plate (e.g. which might correspond to the recessed portion of the main body panel portion of the removable cover). Generally, the raised grip may be located on (e.g. the exterior of, and be a part of) the circular back plate. Typically, the raised grip may project outward away from the removable cover and may intersect the center of the circular back plate (e.g. extend from one end of the circular back plate to the other end of the circular back plate). In some embodiments, the raised grip may comprise a different shape (e.g. other than a line/rectangle) such as an arrow, triangle, diamond, etc. In some embodiments, the key may not include a circular back plate. In this case, the raised grip may fit within the recessed portion of the removable cover and may be operable to rotate without the support of a circular back plate. Generally, the longitudinal member of the key may be configured to run through the through-hole located in the removable cover and through the center of the battery compartment and into a lock-fit aperture located near the backside of the battery compartment. Generally, the distal end of the longitudinal member may comprise a pin. The pin may be (significantly) shorter than the longitudinal member and may have a smaller diameter than the longitudinal member. Additionally, the pin may be configured to attach perpendicularly to the end of the longitudinal member (e.g. to serve a function similar to that of a key). The pin may fit into the lock-fit aperture to lock and unlock the removable cover from the battery compartment. In this manner, the disclosed embodiments may comprise two configurations: an unlocked configuration and a locked configuration.

In this disclosure, the removable cover typically comprises a recessed portion. The exterior portion of the key (e.g. the grip surface) may be configured to snugly fit within the recessed portion. Generally, the recessed portion corresponds with the (grip surface, e.g. raised grip and/or circular back plate of the) key (e.g. such that the circular back plate and/or raised grip fits within the recessed portion), and wherein the grip surface (e.g. circular back plate of the key) may be configured to fit snugly within the recessed portion (e.g. substantially fill the recessed portion and/or be shaped similarly/correspondingly, so as to allow rotation of the key without any interference by the recessed portion). Typically, the grip surface on the key may further comprise a circular back plate (and a raised grip) (configured to provide a larger grip surface area (e.g. larger than merely the raised grip) for the (exterior face of the) key, to facilitate removal of the removable cover from the battery compartment with a gloved hand), wherein the raised grip is mounted on the exterior of the circular back plate (e.g. the circular back plate interfaces with the (central) raised grip), and wherein the circular back plate may be configured to interface/interact with the removable cover (e.g. the circular back plate may be larger than the through-hole in the main body panel portion of the removable cover, and may be configured to allow rotation of the key/circular back plate/raised grip with respect to the main body panel portion of the removable cover).

In the locked configuration of some embodiments, the (central) raised grip of the key is often configured to lay flush with the outer surface of the removable cover (e.g. main body panel portion). In other embodiments, the circular back plate may be configured to lay flush with the outer surface of the removable cover (e.g. main body panel portion), but the raised grip may project outward beyond that outer surface. In the unlocked configuration, the key (pops out automatically and) is biased outward away from the (outer/exterior) surface of the removable cover (e.g. a biasing element is configured with respect to the key so that, in the unlocked position, the key automatically pops outward with respect to the main body panel portion of the removable cover). Generally, the key may be biased outward via a bias element such as a spring. The spring may be located at the center of the recessed portion. Additionally, the spring may be configured to wrap around the longitudinal member of the key (since the longitudinal member of the key is configured to run through the through-hole at the center of the removable cover (located in the recessed portion) and then run through the lock-fit aperture located at the backside of the battery compartment). Thus, when the user rotates the key via the raised grip to unlock the battery compartment, the key is configured to automatically project outward away from the main body panel portion of the removable cover. Typically, this results due to the bias element pushing the key outward once the key is in the unlocked configuration. In some embodiments, the bias element may not necessarily be located at the center (and wrapped around the longitudinal member of the key). The bias element may be located at multiple points/one or more points behind the circular back plate of the grip surface. Alternatively (or additionally), the bias element may be located within the lock-fit aperture located at the back of the battery compartment (e.g. interacting with the distal end of the key). Persons of skill will appreciate other materials, methods, and/or locations to place the bias element to automatically bias the key outward.

Additionally, in some embodiments, the key may further comprise a longitudinal member which comprises an interference element. Typically, two interference elements may be located opposite each other in proximity to the center of the longitudinal member. Generally, the interference element may be configured to fit within a protruding member (located on the back-side/underside/inner surface of the removable cover/main body panel portion) allowing for longitudinal motion (e.g. inward and outward-forward and backward motion (e.g. linear motion) (e.g. not rotational motion)) of the key (e.g. the protruding member acts as (at least a partial) guide rail, allowing longitudinal movement of the pin/distal end of the key (when the interference element interfaces with the protruding member) but preventing rotation of the key (when the interference element interfaces with the protruding member).

In some embodiments, the removable cover may further comprise flexible arms, cavities, and/or protrusions located within the recessed portion. Typically, the flexible arms may prevent the key from being removed (and/or sliding longitudinally) via the through-hole when the key is in the locked configuration (e.g. the pin lying approximately parallel and/or the interference elements not aligning with the protruding member of the removable cover). This may result due to the fact that the flexible arms may be configured to flex/contract inward but not outward. Thus, if the user attempts to pull the key out (e.g. outward) of the through-hole while in the locked configuration, the user may fail at unlocking the removable cover and/or break the parts/elements involved (e.g. removable cover, key, longitudinal member, etc.). In this manner, the flexible arms provide a resistance to prevent the user from inappropriately unlocking/locking the removable cover. Additionally, in some embodiments, the removable cover (e.g. main body panel portion) may comprise one or more cavities located within the recessed portion. Generally, the one or more cavities have corresponding protrusions located on the backside of the key (more specifically, typically located on the backside of the circular back plate of the key). Typically, the one or more protrusions are configured to align (e.g. fit within) with the corresponding number of cavities (to create a firm locked grip) (e.g. to establish a barrier/resistance to overcome when configuring the device to/towards the unlocked configuration) (e.g. the device further comprising a resistance mechanism configured to provide a pre-set amount of resistance with respect to (rotation of the key to) moving from locked to unlocked configuration). In some embodiments, the key may comprise one or more cavities while the main body panel portion (within the recessed portion) of the removable cover may comprise a corresponding number of protrusions. In other words, the location of the cavities and the protrusions may be switched in some embodiments. Persons of skill will appreciate other forms of adding resistance to the removable cover of the battery compartment to ensure the user does not improperly lock/unlock the removable cover, break the parts involved, and/or to prevent accidental removal of the removable cover from the battery compartment.

Generally, the battery compartment may comprise a lock-fit/corresponding aperture, linking element, and/or welding. In some embodiments, the lock-fit aperture may be located on the innermost portion (e.g. back-wall) of the battery compartment/recessed body (e.g. behind the batteries) and/or between the battery locations—so that the longitudinal member of the key may extend between the batteries in operation when the cover is locked in place and the batteries are in the battery compartment. Typically, the linking element (such as a rubber string) may connect the removable cover to the battery compartment (e.g. to ensure the removable cover remains attached to the hearing protection device even in the unlocked configuration; e.g. to prevent the removable cover from being lost), and the linking mechanism typically provides enough play/slack so that the removable cover can, in the unlocked configuration, be moved clear of the opening for the recessed body of the battery compartment (to allow access for changing of batteries). Also, to prevent communication of air between the battery compartment and the inside of the ear cup (and to maintain sound attenuation of the hearing protection device), the battery compartment may be welded (e.g. via ultrasonic welding) in place within the ear cup (shell) (to prevent/minimize reduction in Noise Reduction Rating (NRR) level of ear cup). Generally, the welding would result in an airtight mounting of the battery compartment recessed body in the ear cup, and may take place on the interior side of the battery compartment (e.g. the side of the battery compartment comprising the processor). While persons of skill should understand the disclosed embodiments based on the above disclosure, the following figures may provide specific examples that may further clarify the disclosure.

Figure 2A:
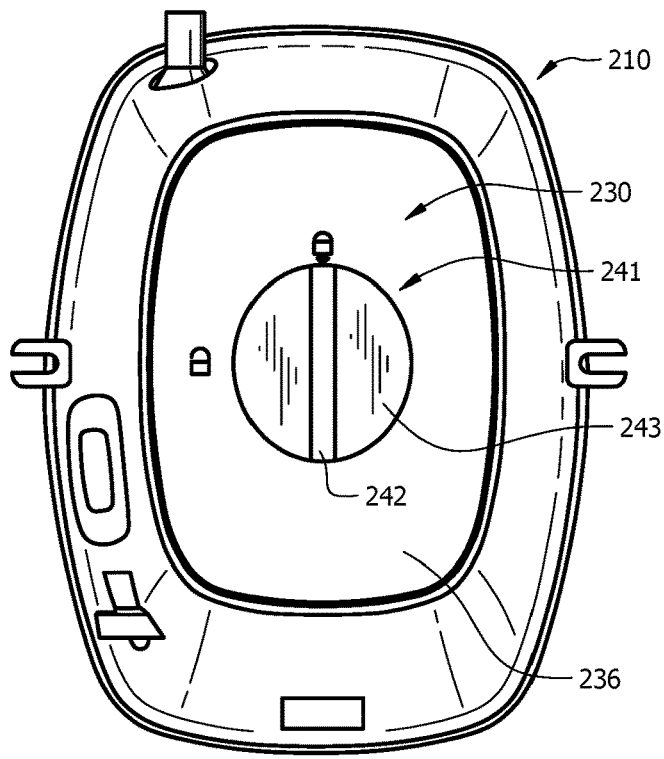
FIG. 2A illustrates a front view of an exemplary embodiment of an ear cup comprising a removable cover and a key in a locked configuration.

Turning now to the drawings, FIG. 1 illustrates a perspective view of an exemplary embodiment of a hearing protection device 100 comprising one or more ear cups 110. In the embodiment of FIG. 1, at least one ear cup 110 comprises a battery compartment 120, a removable cover 130, and a key. In some embodiments, the battery compartment 120 may be configured for 2 AA batteries as shown in the embodiment of FIG. 1. In other embodiments, the battery compartment 120 may be configured for other variations of batteries (e.g. AAA batteries, C batteries, D batteries, etc.). Generally, the battery compartment 120 may be located within one ear cup 110 of the hearing protection device 100 (e.g. earmuff), but in some embodiments it may be located on both ear cups 110. As shown in FIG. 1, the battery compartment 120 may be fully enclosed/encompassed within and not extending out of the ear cup 110. Generally, the battery compartment 120 would include a removable cover 130. The removable cover 130 in the embodiment of FIG. 1 comprises a key and is shown in the unlocked configuration (e.g. with the key projecting outward away from the removable cover 130) (e.g. with the removable cover 130 detached from the battery compartment 120 of the hearing protection device 100). Typically, the key comprises a gripping surface 141. The gripping surface 141 shown in the embodiment of FIG. 1 comprises a circular back plate 143 and a raised grip 142. In the embodiment of FIG. 1, the circular back plate 143 of the key is operable to fit within (e.g. correspond to) a recessed portion 132 of the removable cover 130. Typically, the circular back plate 143 of the key fits snugly within the recessed portion 132, and (in the locked configuration) the circular back plate 143 may lay flush with the main body panel portion 136 (e.g. outer surface) of the removable cover 130. The raised grip 142 is configured to allow the user to use his/her fingers (or gloved hands) to grasp the raised grip 142 and rotate the key. Typically, the raised grip 142 is configured to protrude outwards away from the ear cup 110 so that the user may find the raised grip 142 without difficulty (e.g. by feel). However, the raised grip 142 typically does not protrude outwards too significantly to prevent interference with the user's activities while the hearing protection device 100 is being used (e.g. the raised grip 142 getting tangled with the user's hair, clothes, personal protective equipment (PPE), nearby equipment, etc.). So typically, the raised grip might protrude from 3-5 millimeters. Additionally, the raised grip 142 may be configured to rotate (e.g. by 90 degrees as shown in the embodiment of FIG. 1). In the embodiment of FIG. 1, a 90 degree clockwise rotation may place the key in a locked configuration. The configuration shown in the embodiment of FIG. 1 with the raised grip 142 lying approximately horizontally indicates the key is in an unlocked configuration (see also FIG. 2B). In some embodiments, the key may require a greater (e.g. greater than 90 degrees) or lesser (e.g. lesser than 90 degrees) rotation in another direction (e.g. counter-clockwise or clockwise). Thus, in some embodiments, the raised grip 142 may not have to be aligned (approximately) horizontally for the removable cover 130 of the hearing protection device 100 to be in the unlocked configuration. Similarly, in some embodiments, the raised grip 142 may not have to be aligned (approximately) vertically for the battery compartment 120 of the hearing protection device 100 to be in the locked configuration (for example, as shown in FIG. 2A). Additionally, shown in the embodiment of FIG. 1, the recessed portion 132 of the removable cover 130 may comprise a cavity 131. In some embodiments, there may be one or more cavities 131 located within the recessed portion 132 of the main body panel portion 136 of the removable cover 130. Generally, the one or more cavities 131 have corresponding protrusions located on the backside of the key (more specifically, located on the backside of the circular back plate 143 of the key—see for example FIG. 4B). Typically, the one or more protrusions are configured to align (e.g. fit within) with the corresponding number of cavities 131 (to create a firm locked grip) (e.g. to establish a barrier/resistance to overcome when configuring the hearing protection device 100 to/towards the unlocked configuration) (e.g. the hearing protection device further comprising a resistance mechanism configured to provide a pre-set amount of resistance with respect to (rotation of the key to) moving from locked to unlocked configuration).

FIG. 2A illustrates a front view of an exemplary embodiment of an ear cup 210 comprising a removable cover 230 having a main body panel portion 236 and a key in a locked configuration. As shown in the embodiment of FIG. 1, the key shown in the embodiment of FIG. 2A is centrally located on the removable cover 230 with the main body panel portion 236 surrounding the key and comprises a gripping surface 241. In the embodiment of FIG. 2A, the gripping surface 241 comprises a circular back plate 243 and a raised grip 242. The circular back plate 243 and the raised grip 242 may function similar to the circular back plate 143 and raised grip 142 discussed in reference to the embodiment of FIG. 1. However, in the embodiment of FIG. 2A, the raised grip 242 is aligned vertically, indicating the removable cover 230 is locked to the battery compartment of the ear cup 210. In some embodiments, the removable cover 230 (e.g. the main body panel portion 236) may be slightly curved inward (e.g. indented) or inset to allow the user to more easily find the removable cover 230 by touch (for example, if the user is wearing the hearing protection device and is not able to see the ear cup 210). Additionally, the raised grip 242 on the grip surface 241 of the key (which projects outward above the outer surface of the main body panel portion 236 of the removable cover 230) may make it easier for the user to find the key to unlock and lock the removable cover 230. In the embodiment of FIG. 1, the circular back plate 243 of the grip surface 241 is configured to lay flush with the surrounding main body panel portion 236 (when in locked configuration). In some embodiments, the circular back plate 243 may protrude outwards or be inset within the recessed portion of the removable cover 230.

Figure 2B:
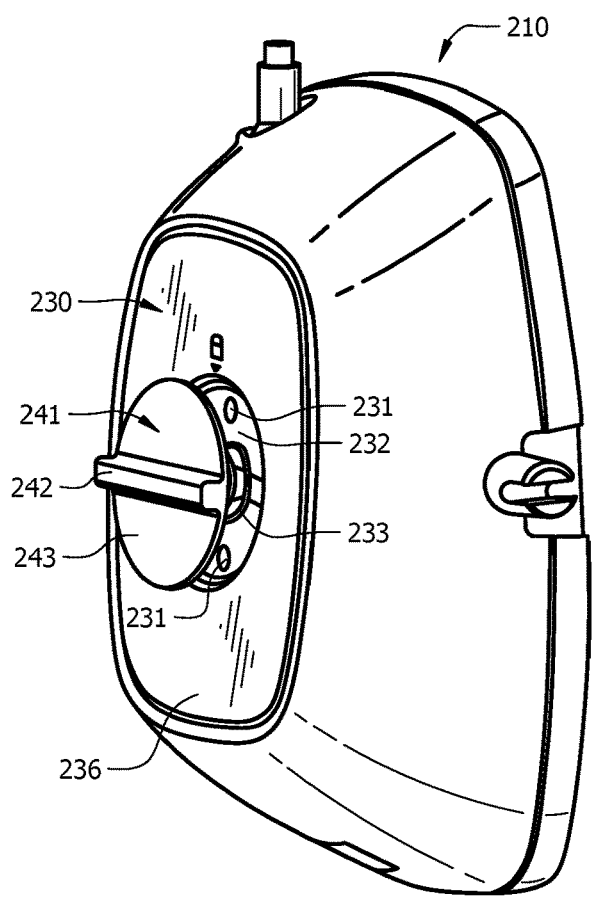
FIG. 2B illustrates a side view of an exemplary embodiment of an ear cup comprising a removable cover, a key, and a bias element in an unlocked configuration.

FIG. 2B illustrates a side perspective view of an exemplary embodiment of an ear cup 210 comprising a removable cover 230, a key, and a bias element 233 in an unlocked configuration. In the embodiment of FIG. 2B, the key is biased outward away from the removable cover 230 by the bias element 233. In FIG. 2B, the bias element 233 is located within the recessed portion 232 of the removable cover 230 (e.g. between the main body panel portion and the circular back plate). More specifically, the bias element 233 shown in the embodiment of FIG. 2B is a spring and is located at the center of the recessed portion 232. Additionally, the spring in the embodiment of FIG. 2B is configured to wrap around the longitudinal member of the key (since the longitudinal member of the key is configured to run through the through-hole at the center of the removable cover (located in the recessed portion 232) and then run through the lock-fit aperture located at the backside of the battery compartment—when in locked configuration). Thus, when the user rotates the key via the raised grip 242 shown in the embodiment of FIG. 2B and unlocks the battery compartment, the key is configured to automatically project (e.g. pop) outward away from the main body panel portion 236 of the removable cover 230. Typically, this results due to the bias element 233 pushing the key outward once the key is in the unlocked configuration. In some embodiments, the bias element 233 may not necessarily be located at the center (and wrapped around the longitudinal member of the key). The bias element 233 may be located at one or more points behind the circular back plate 243 of the grip surface 241. Also, the bias element 233 may alternatively be located within the lock-fit aperture located at the back of the battery compartment in other embodiments. Additionally, in FIG. 2B, there exist two cavities 231. The cavities 231 function similar to the cavities 131 shown in the embodiment of FIG. 1. Typically, there may be two cavities 231 located opposite of each other (about the key) as shown in the embodiment of FIG. 2B. In some embodiments, the number of cavities 231 may vary depending on what a person of skill deems reasonable.

Figure 2C:
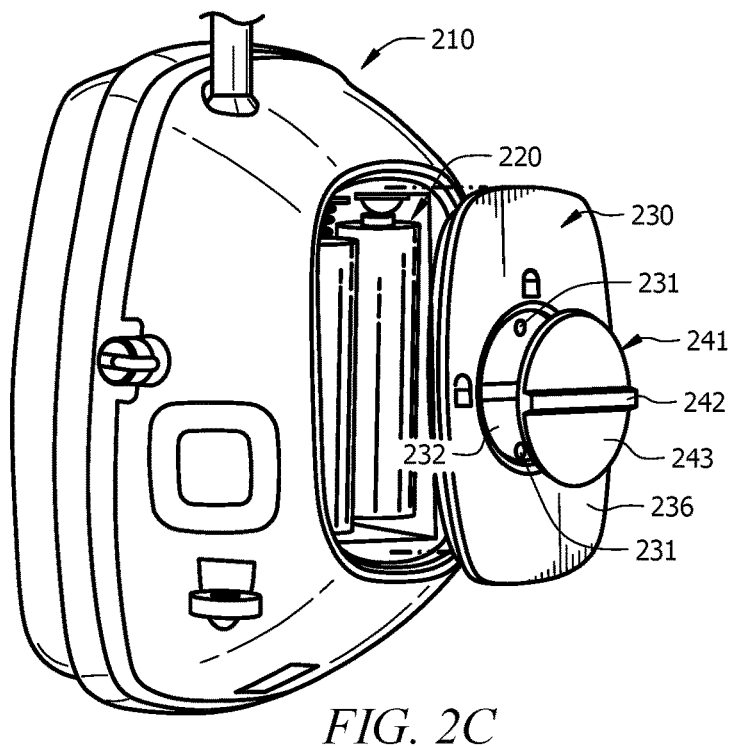
FIG. 2C illustrates a side view of an exemplary embodiment of an ear cup, similar to the embodiment shown in FIG. 2B, with the key biased outward away from the removable cover and the removable cover detached from the battery compartment.

FIG. 2C illustrates a side view of an exemplary embodiment of an ear cup 210, similar to the embodiment shown in FIG. 2B, with the key biased outward away from the removable cover 230 and the removable cover 230 detached from the battery compartment 220 (e.g. recessed body). In the embodiment of FIG. 2C, the removable cover 230 comprising the key functions/performs in a similar manner as discussed in reference to FIG. 1 above. Additionally, the elements of the removable cover 230 (e.g. main body panel portion 236, one or more cavities 231, recessed portion 232, bias element, through-hole, etc.) and the elements of the key (e.g. grip surface 241, raised grip 242, circular back plate 243, longitudinal member, pin, etc.) may also perform similarly to the embodiment shown in FIG. 1. In the embodiment of FIG. 2C, the battery compartment 220 comprises 2 AA batteries. In other embodiments, the battery compartment 220 may be configured for other variations of batteries (e.g. AAA batteries, C batteries, D batteries, etc.). Generally in the embodiment of FIG. 2C, the battery compartment 220 comprises a lock-fit aperture (not shown, but located near the backside of the recessed body and between the two batteries allowing the longitudinal member of the key to fit into the lock-fit aperture) (located on the innermost portion (e.g. back-wall) of the battery compartment 220 (e.g. behind the batteries) and/or between the battery locations—so that the longitudinal member of the key may extend between the batteries in operation when the removable cover 230 is locked in place and the batteries are in the battery compartment 220). Typically, the longitudinal member (not shown) of the key comprises a pin located at the end of the key. The pin may be configured to run perpendicularly to the longitudinal member. Thus, once the pin is inserted into the lock-fit aperture, the user may rotate the key to lock the removable cover 230 to the battery compartment 220. In other words, the pin is shaped to interact/correspond with the lock-fit/corresponding aperture to provide two configurations for the removable cover 230: the unlocked configuration and the locked configuration.

FIG. 3A-FIG. 3D illustrate an alternative exemplary embodiment of an ear cup 310 comprising a removable cover 330 and a key similar to the exemplary embodiments shown in the figures discussed above. However, in the exemplary embodiments of FIG. 3A-FIG. 3D, the key differs in configuration (e.g. the key does not comprise a circular back plate, but merely includes a raised grip). Thus, for the key to function/perform adequately, other elements such as the bias element may vary as well. The exemplary embodiments shown in FIG. 3A-FIG. 3D will be discussed in more detail below.

Figure 3A:
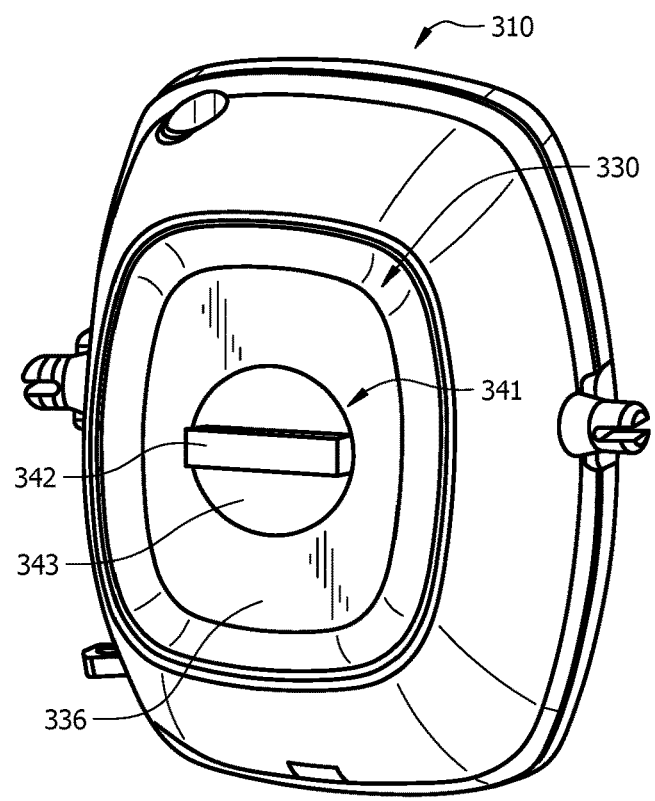
FIG. 3A illustrates a front view of an exemplary embodiment of an ear cup comprising a removable cover and a key in a locked configuration.

FIG. 3A illustrates a front view of an exemplary embodiment of an ear cup 310 comprising a removable cover 330 having a main body panel portion 336 and a key in a locked configuration (e.g. the raised grip 342 lying approximately horizontally). As shown in the previous embodiments of FIG. 1-FIG. 2C, the key shown in the embodiment of FIG. 3A is centrally located on the main body panel portion 336 of the removable cover 330. In the embodiment of FIG. 3A, the gripping surface 341 comprises a raised grip 342 (in the embodiments of FIG. 1-FIG. 2C, the gripping surface 341 further comprised a circular back plate). The raised grip 342 may be configured to extend/project outward away from the hearing protection device (e.g. outward from the outer surface of the ear cup 310 and/or outward/away from the user's ears when the user is wearing the hearing protection device). Additionally, the raised grip 342 may be configured to lie entirely within the recessed portion 332 of the removable cover 330 so as to be flush with the outer surface of the removable cover 330. In other embodiments, the raised grip 342 may be configured to lie entirely within the recessed portion 332 (but perhaps be a bit indented from the outer surface). It is also important to note that the raised grip 342 may not necessarily be configured to lay approximately horizontally to place the removable cover 330 in the locked configuration. In some embodiments, the raised grip 342 may be configured to lay in another orientation (e.g. vertically) to be placed in the locked configuration. The orientation of the raised grip 342 may vary as long as it is pre-configured and the user may not change the orientation of the locked configuration and the unlocked configuration during use of the hearing protection device. In the embodiment of FIG. 3A, the raised grip 342 is shown to be a bit indented from the outer surface but lies completely within the recessed portion 33 of the removable cover 330 (although in other embodiments, the raised grip may be flush or project slightly outward from the recessed portion). In some embodiments, the recessed portion 332 of the removable cover 330 may exist to allow the user to easily find the key to detach/attach the removable cover 330 by feeling around the ear cup 310 (rather than having to look for it (e.g. removing the hearing protection device from the user's ears)). Also, in some embodiments, the shape of the raised grip 342 of the key may vary. The shape may be an arrow, triangle, rhombus, etc. Additionally, in some embodiments, the main body panel portion 336 of the removable cover 330 may be slightly curved inward and/or inset allowing the user to more easily find the removable cover 330 by touch (for example, if the user is wearing the hearing protection device and is not able to see the ear cup 310). Additionally, the raised grip 342 on the grip surface 341 of the key may make it easier for the user to find the key to unlock and lock the removable cover 330.

Figure 3B:
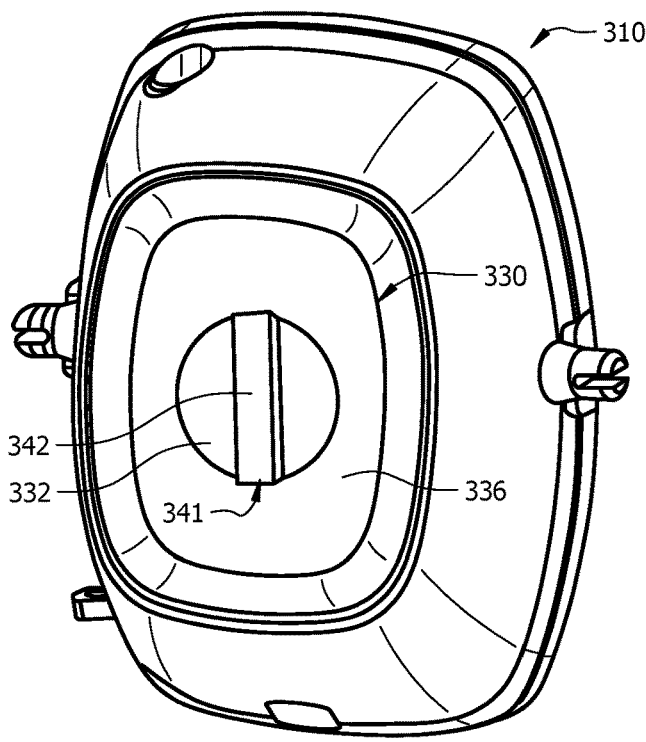
FIG. 3B illustrates a front view of an exemplary embodiment of an ear cup, similar to the embodiment shown in FIG. 3A, with the key in an unlocked configuration.

FIG. 3B illustrates a front view of an exemplary embodiment of an ear cup 310 comprising a removable cover 330 having a main body panel portion 336 and a key in an unlocked configuration (e.g. the raised grip 342 lying approximately vertically). The elements of the exemplary embodiment shown in FIG. 3B (e.g. ear cup 310 comprising a removable cover 330, a main body panel portion 336, a key, a recessed portion 332, a raised grip 342, a grip surface 341, etc.) interact/operate in a similar manner to the elements discussed in reference to the exemplary embodiment of FIG. 3A above. In FIG. 3B, however, the key has been turned to the unlocked configuration, so that the key may now be used to assist in removing the removable cover 330 (as discussed below with regards to FIG. 3C-FIG. 3D).

Figure 3C:
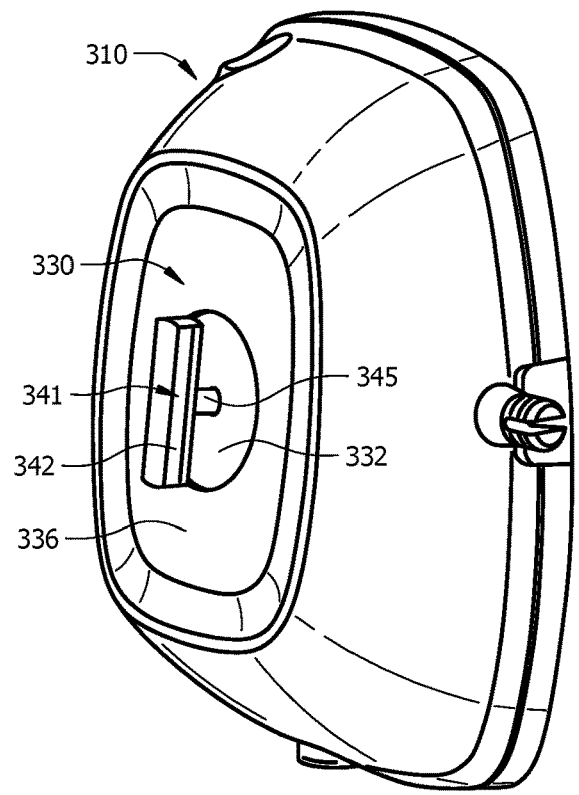
FIG. 3C illustrates a side view of an exemplary embodiment of an ear cup, similar to the embodiments shown in FIG. 3A-FIG. 3B, with the key biased outward away from the removable cover and in an unlocked configuration.

FIG. 3C illustrates a side perspective view of an exemplary embodiment of an ear cup 310 comprising a removable cover 330 and a key (similar to the exemplary embodiment shown in FIG. 3B) in an unlocked configuration. In the embodiment of FIG. 3C, the key is biased outward away from the removable cover 330 by a bias element. Typically, the bias element may be located within the recessed portion 332 of the removable cover 330 (e.g. between the raised grip 342 and the main body panel portion 336 of the removable cover 330). In some embodiments, the bias element may be located at multiple points/one or more points behind the raised grip 342. Alternatively, the bias element may be located within the lock-fit aperture located at the back of the battery compartment (e.g. interacting with the distal end of the key to bias the key outward). More specifically, the bias element shown in the embodiment of FIG. 3C is a spring and is located within the lock-fit aperture located at the back of the battery compartment. Thus, when the user rotates the key via the raised grip 342 shown in the embodiment of FIG. 3C and unlocks the battery compartment, the key is configured to automatically project outward away from the main body panel portion 336 of the removable cover 330. Typically, this results due to the bias element pushing the key outward once the key is in the unlocked configuration. In some embodiments, the key may not be biased outward (for example, if the embodiment of FIG. 3C did not include a spring), and the user might instead pull the key outward upon unlocking it (e.g. turning the raised grip to the unlocked configuration). Additionally, similar to the exemplary embodiments shown in FIG. 1-FIG. 2C, the key is configured to be attached to the main body panel portion 336 in a manner allowing the key to slide longitudinally with respect to the main body panel portion 336 (while remaining (permanently) attached at all times (e.g. because the distal end of the key (and the raised grip 342) is larger than the hole/opening in the main body panel portion 336 through which the longitudinal member 345 of the key passes (e.g. through-hole)))). However, unlike the exemplary embodiments shown in FIG. 1-FIG. 2C, the exemplary embodiment of FIG. 3C does not comprise cavities. In other words, the exemplary embodiment of FIG. 3C does not comprise an additional barrier/resistance to overcome when configuring the device to/towards the unlocked configuration.

Figure 3D:
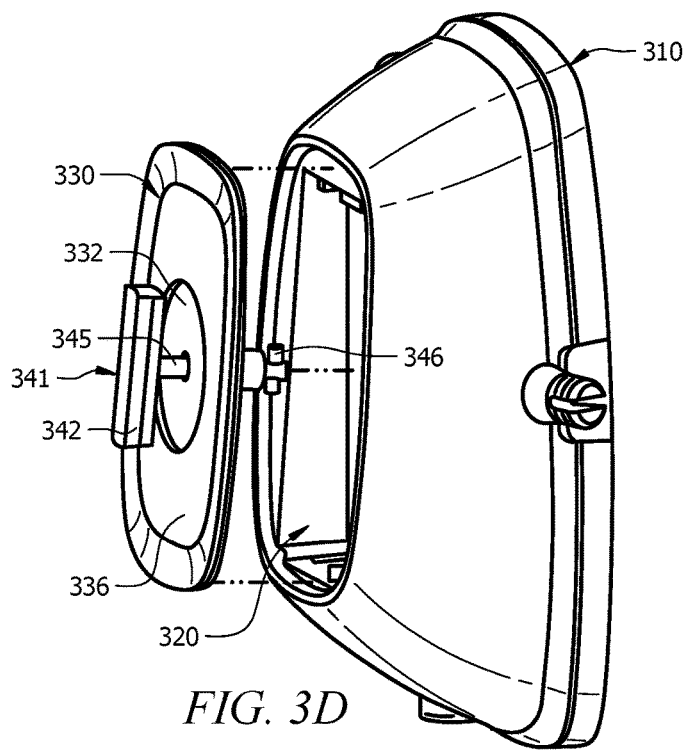
FIG. 3D illustrates a side view of an exemplary embodiment of an ear cup, similar to the embodiments shown in FIG. 3A-FIG. 3C, with the key biased outward away from the removable cover and in an unlocked configuration and the removable cover detached from the battery compartment.

FIG. 3D illustrates a side perspective view of an exemplary embodiment of an ear cup 310, similar to the embodiments shown in FIG. 3A-FIG. 3C, with the key biased outward away from the removable cover 330, in an unlocked configuration, and the removable cover 330 detached from the battery compartment 320. The elements of the exemplary embodiment shown in FIG. 3D (e.g. ear cup 310 comprising a removable cover 330, a main body panel portion 336, a key, a recessed portion 332, a raised grip 342, a grip surface 341, a battery compartment 320, etc.) interact/operate in a similar manner to the elements discussed in reference to the exemplary embodiments of FIG. 3A-FIG. 3C above. In the exemplary embodiment of FIG. 3D, it can be further seen that the key comprises a longitudinal member 345 configured to run through the through-hole of the removable cover, through the center of the battery compartment 320 (e.g. between two batteries), and into the corresponding/lock-fit/ lock-fit aperture (when in the locked configuration). Additionally, in the exemplary embodiment of FIG. 3D, the key comprises a longitudinal member 345 which further comprises a pin 346 (e.g. the pin 346 forms the distal end of the key and may run perpendicular to the longitudinal member 345), and wherein the pin 346 is configured to lock into the lock-fit aperture (so that without further rotation to the unlocked configuration, the key will not move longitudinally). Typically, the shape of the pin 346 is configured to correspond to the shape of the lock-fit aperture.

Figure 4A:
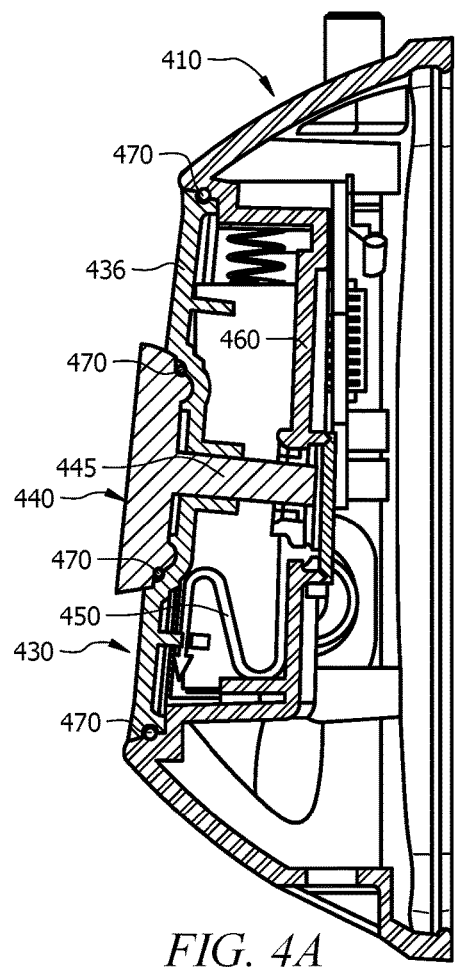
FIG. 4A illustrates a cross-sectional view of an exemplary embodiment of an ear cup comprising a removable cover, a welded interior cover, a linking element, and a key in a locked configuration.

FIG. 4A illustrates a cross-sectional view of an exemplary embodiment of an ear cup 410 (similar to that of FIG. 1, for example) comprising a removable cover 430, a welded interior cover 460 (e.g. recessed body), a linking element 450, and a key 440 in a locked configuration. As shown in the exemplary embodiment of FIG. 4A, the key 440 is configured to be attached to the main body panel portion 436 of the removable cover 430 in a manner allowing the key to slide longitudinally with respect to the main body panel portion 436 (while remaining (permanently) attached at all times (e.g. because the distal end of the key 440 (and the raised grip) is larger than the hole/opening in the main body panel portion 436 through which the longitudinal member 445 of the key passes 440 (e.g. through-hole)))). Additionally, in the exemplary embodiment of FIG. 4A, the ear cup 410 may also comprise a linking element 450 (located within the battery compartment) which connects the removable cover 430 to the battery compartment so that the user may not potentially lose the removable cover 430 (e.g. to ensure the removable cover 430 remains attached to the hearing protection device even in the unlocked configuration; e.g. to prevent the removable cover 430 from being lost), and wherein the linking element 450 provides enough play/slack so that the removable cover 430 can, in the unlocked configuration, be moved clear of the opening for the recessed body of the battery compartment (to allow access for changing of batteries). Also, to prevent communication of air between the battery compartment and the inside of the ear cup 410 (and to maintain sound attenuation of the hearing protection device), the battery compartment (e.g. recessed body) may be welded (e.g. via ultrasonic welding) in place within the ear cup (shell) (to prevent/ minimize reduction in Noise Reduction Rating (NRR) level of ear cup) (as shown in the exemplary embodiment of FIG. 4A). As further barrier from water and air communication, the hearing protection device may comprise one or more sealing elements 470. In some embodiments, a first sealing element may be located between the removable cover 430 and the ear cup 410 (e.g. around the circumference/lip/interface). In some embodiments, a second sealing element may be located between the grip surface of the key 440 and the main body panel portion 436 of the removable cover 430 (e.g. to prevent water and/or air from entering the hearing protection device (e.g. International Protection (IP) rating of IP54; IP54 is a classification designated to devices which prevent water from being sprayed into the device from any direction). Typically, the first seal is located on either the outer edge circumference of the main body panel portion 436 of the removable cover 430 or on the circumference of the opening of the recessed body of the battery compartment (which interfaces with the circumference of the main body panel portion 436 of the removable cover 430). Typically, the second seal is located on either the outer edge circumference of the grip surface of the key 440 or on the circumference of the recessed portion of the main body panel portion 436 of the removable cover 430 (which interfaces with the circumference of the grip surface of the key 440). In the embodiment of FIG. 4A, the ear cup comprises 410 both the first seal and the second seal.

Figure 4B:
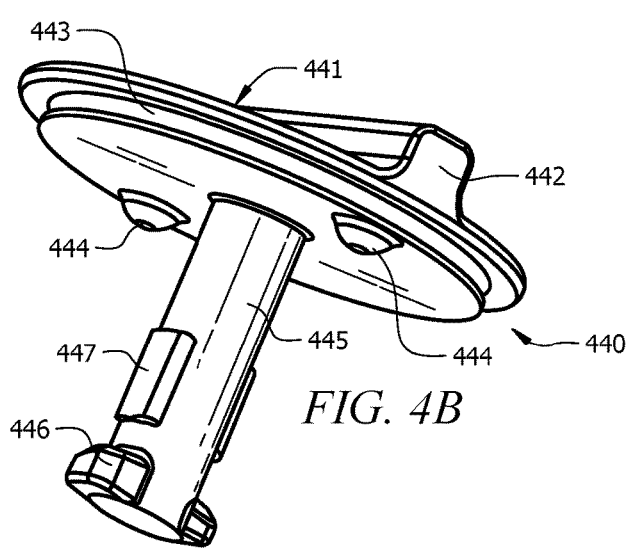
FIG. 4B illustrates a perspective view of an exemplary embodiment of a key comprising a raised grip, a circular back plate, two protrusions, a longitudinal member, a pin, and two interference elements.

FIG. 4B illustrates a perspective view of an exemplary embodiment of a key 440 (similar to that of FIGS. 1, 2A, 2B, and 4) comprising a grip surface 441 (further comprising a raised grip 442 and a circular back plate 443), two protrusions 444, a longitudinal member 445, a pin 446, and two interference elements 447. Typically, the grip surface 441 comprises a (central) raised grip 442 which extends/projects outward away from the hearing protection device (e.g. outward from the outer surface of the ear cup and/or outward/away from the user's ears when the user is wearing the hearing protection device), and a circular back plate 443 (configured to provide a larger grip surface 441 area (e.g. larger than merely the raised grip 442) for the (exterior face of the) key 440, to facilitate removal of the removable cover from the battery compartment with a gloved hand). Generally, the raised grip 442 is mounted on the exterior of the circular back plate 443 (e.g. the circular back plate 443 interfaces with the (central) raised grip 442), and wherein the circular back plate 443 is configured to interface/interact with the removable cover (e.g. the circular back plate 443 is larger than the opening in the main body panel portion of the removable cover, and is configured to allow rotation of the key 440/circular back plate 443/raised grip 442 with respect to the main body panel portion of the removable cover). Additionally, the key 440 may comprise one or more protrusions 444 located on the backside/underside of the circular back plate 443 of the key 440, wherein the corresponding number of cavities are located within the recessed portion of the main body panel portion of the removable cover, and wherein, in the locked configuration, the one or more protrusions 444 are configured to align (e.g. fit within) with the corresponding number of cavities (to create a firm locked grip) (e.g. to establish a barrier/resistance to overcome when configuring the device to/towards the unlocked configuration) (e.g. the device further comprising a resistance mechanism configured to provide a pre-set amount of resistance with respect to (rotation of the key 440 to) moving from locked to unlocked configuration. In some embodiments, the key 440 may comprise one or more cavities while the main body panel portion (within the recessed portion) of the removable cover may comprise a corresponding number of protrusions 444. In other words, the location of the cavities and the protrusions may be switched in some embodiments. Also shown in the embodiment of FIG. 4B, the key 440 may comprise a longitudinal member 445 configured to function/perform similarly to the longitudinal member 445 shown in previous exemplary embodiments of FIG. 1-FIG. 4A. The longitudinal member 445 may further comprise a pin 446 (e.g. at the distal end of the key) and two interference elements 447. The interference elements 447 may be configured to fit within a protruding member (located on the back-side/underside/inner surface of the removable cover) allowing for longitudinal motion (e.g. inward and outward-forward and backward motion (e.g. linear motion) (e.g. not rotational motion)) of the key 440 (e.g. the protruding member acts as (at least a partial) guide rail, allowing longitudinal movement of the pin 446 (when the interference element 447 interfaces with the protruding member) but preventing rotation of the key 440 (when the interference element 447 interfaces with the protruding member). The pin 446 may form the distal end of the key 440 and be configured to fit within the (lock-fit/corresponding/lock-fit) aperture of the battery compartment to lock and unlock the removable cover from the battery compartment.

Figure 4C:
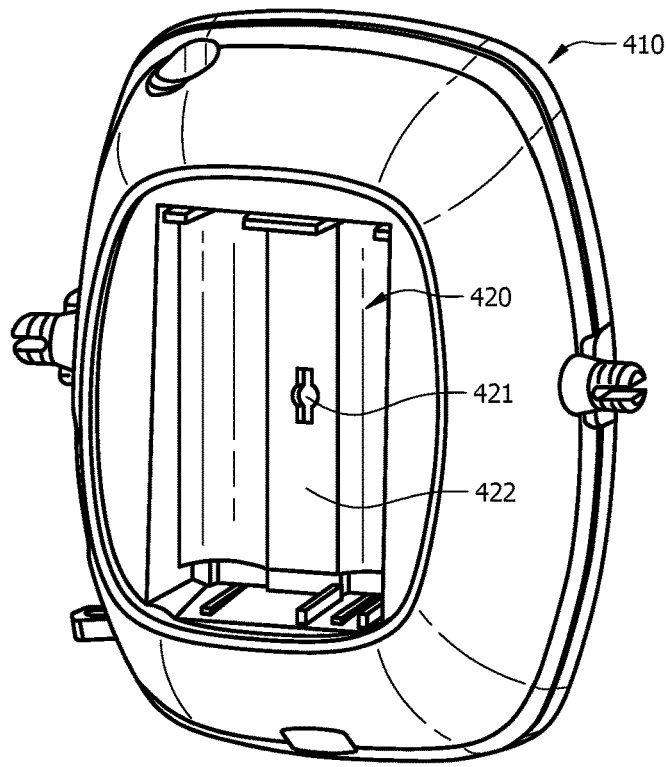
FIG. 4C illustrates a front view of an exemplary embodiment of an ear cup comprising a battery compartment which further comprises a lock-fit aperture.

FIG. 4C illustrates a front view of an exemplary embodiment of an ear cup 410 comprising a battery compartment 420 (e.g. recessed body—for example similar to FIGS. 1, 2C, 3D, and 4A) which further comprises a lock-fit aperture 421. In the embodiment of FIG. 4C, the battery compartment 420 is configured to fit 2 AA batteries. In some embodiments, the battery compartment 420 may be configured to fit a varying number of different types of batteries such as AA, AAA, C, or D batteries. In the embodiment of FIG. 4C, the lock-fit aperture 421 is located on the innermost portion (e.g. back-wall) of the battery compartment 420 (e.g. in recessed body behind the batteries) and/or between the battery locations—so that the longitudinal member of the key may extend between the batteries in operation when the cover is locked in place and the batteries are in the battery compartment 420.

Figure 4D:
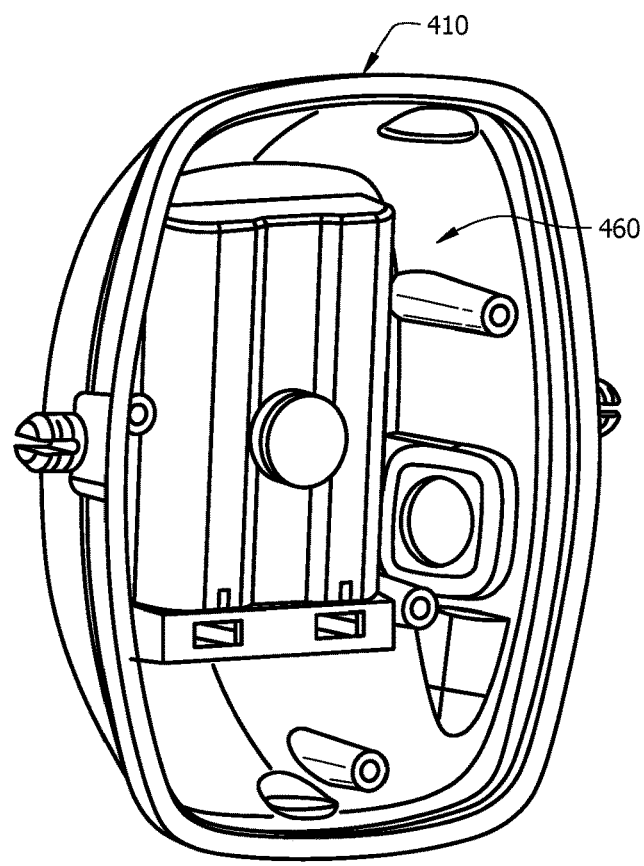
FIG. 4D illustrates an interior view of an exemplary embodiment of an ear cup (the back side of the embodiment shown in FIG. 4C) comprising a welded interior cover.

FIG. 4D illustrates an interior view of an exemplary embodiment of an ear cup 410 (e.g. the back side of the embodiment shown in FIG. 4C) comprising a welded interior cover 460 of the recessed body of the battery compartment with regards to the ear cup. The welded interior cover 460 functions similarly to the welded interior cover 460 shown in the exemplary embodiment of FIG. 4A. In other words, the welded interior cover 460 is configured to prevent communication of air between the battery compartment and the inside of the ear cup 410 (and to maintain sound attenuation of the hearing protection device) (to prevent/minimize reduction in Noise Reduction Rating (NRR) level of ear cup).

FIG. 5A-FIG. 8 illustrate an exemplary embodiment of a removable cover for an ear cup. These figures illustrate the varying key configurations which exist while the device is being configured from an unlocked configuration to a locked configuration or vice versa. Thus, the exemplary embodiments shown in FIG. 5A-FIG. 8 will walk through how the key operates and will be discussed in more detail below.

Figure 5A:
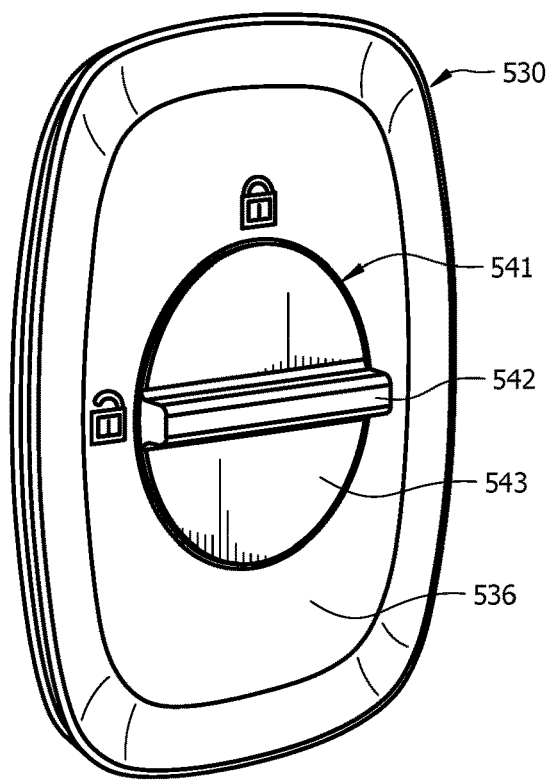
FIG. 5A illustrates a front view of an exemplary embodiment of a removable cover comprising a key in the unlocked configuration.

FIG. 5A illustrates a front view of an exemplary embodiment of a removable cover 530 comprising a key in the unlocked configuration (e.g. the raised grip 542 of the key lying horizontally). FIG. 5A illustrates an ear cup 530 similar to the one shown in the exemplary embodiment of FIG. 2A. However, in FIG. 2A the raised grip 542 lies vertically in the locked configuration. Regardless, the elements shown in the embodiment of FIG. 2A are similar to the elements shown in the embodiment of FIG. 5A. The key is shown to be centrally located on the removable cover 530 with the main body panel portion 536 surrounding the key and comprises a gripping surface 541. In the embodiment of FIG. 5A, the gripping surface 541 comprises a circular back plate 543 and a raised grip 542. The circular back plate 543 and the raised grip 542 may function similar to the circular back plate 543 and raised grip 542 discussed in reference to the embodiment of FIG. 1.

Figure 5B:
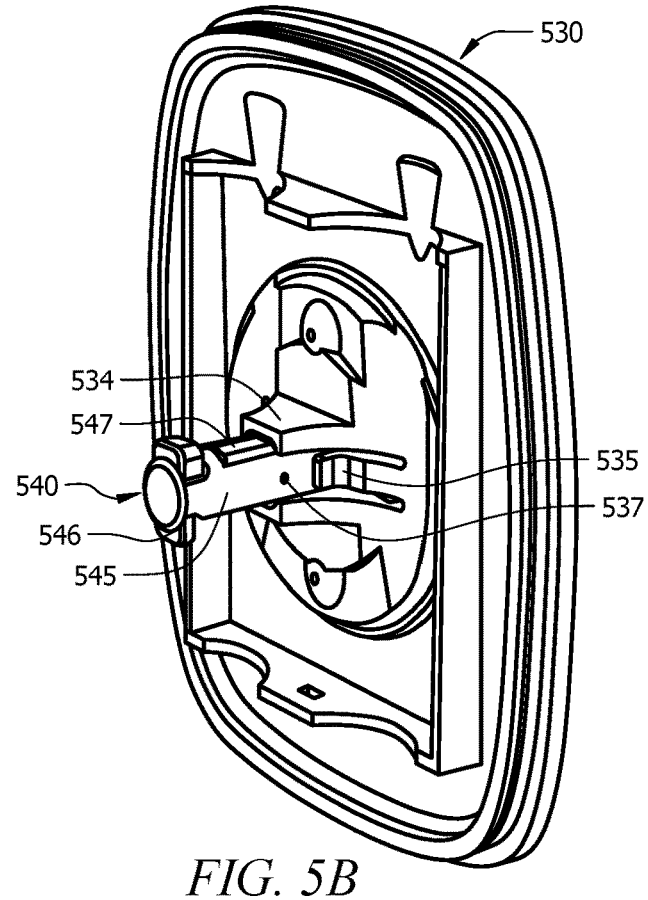
FIG. 5B illustrates a back/interior view of an exemplary embodiment of a removable cover comprising a key in the unlocked configuration, similar to the embodiment shown in FIG. 5A.

FIG. 5B illustrates a back/interior view of an exemplary embodiment of a removable cover 530 comprising a key 540 in the unlocked configuration, similar to the embodiment shown in FIG. 5A. In the exemplary embodiment of FIG. 5B (in the unlocked configuration), the interference elements 547 located on the longitudinal member 545 are shown to align with the protruding member (e.g. guide rail) located on the back-side/underside/inner surface of the removable cover 530. This may allow the longitudinal member 545 of the key 540 to move inward and outward (e.g. forward and backward motion, linear motion, not rotational motion). Once the interference element 547 is fit within the protruding member 534 of the removable cover 530, the key 540 may not be rotated (until the user depresses the key 540 back into the battery compartment). In the unlocked configuration, the pin 546 may be pulled out of the lock-fit aperture located at the back of the battery compartment (as shown in the embodiment of FIG. 4C). Additionally, the removable cover 530 may comprise flexible arms 535 as shown in the exemplary embodiment of FIG. 5B. The flexible arms 535 may prevent the key 540 from being removed via the through-hole 537 when the key 540 is in the locked configuration (e.g. the pin 546 lying approximately parallel and/or the interference elements 547 not aligning with the protruding member 534 of the removable cover 530). This may result due to the fact that the flexible arms 535 may be configured to flex/contract inward but not outward. Thus, if the user attempts to pull the key 540 out of the through-hole while in the locked configuration, the user may fail at unlocking the removable cover 530 and/or break the parts/elements involved (e.g. removable cover 530, key 540, longitudinal member 545, etc.).

Figure 6A:
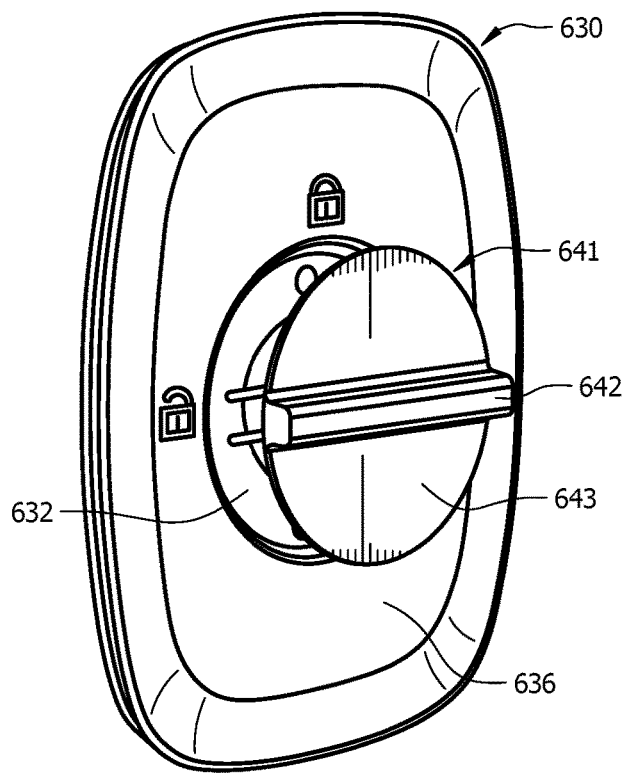
FIG. 6A illustrates a front view of an exemplary embodiment of a removable cover comprising a key in the unlocked configuration and biased outward away from the removable cover.

FIG. 6A illustrates a front view of an exemplary embodiment of a removable cover 630 comprising a key in the unlocked configuration and biased outward away from the removable cover 630. The exemplary embodiment shown in FIG. 6A is similar to the exemplary embodiment shown in FIG. 5A wherein the key is shown to be centrally located on the recessed portion 632 of the removable cover 630 with the main body panel portion 636 surrounding the key and the key comprising a gripping surface 641. In the embodiment of FIG. 6A, the gripping surface 641 comprises a circular back plate 643 and a raised grip 642. The circular back plate 643 and the raised grip 642 may function similar to the circular back plate 143 and raised grip 142 discussed in reference to the embodiment of FIG. 1.

Figure 6B:
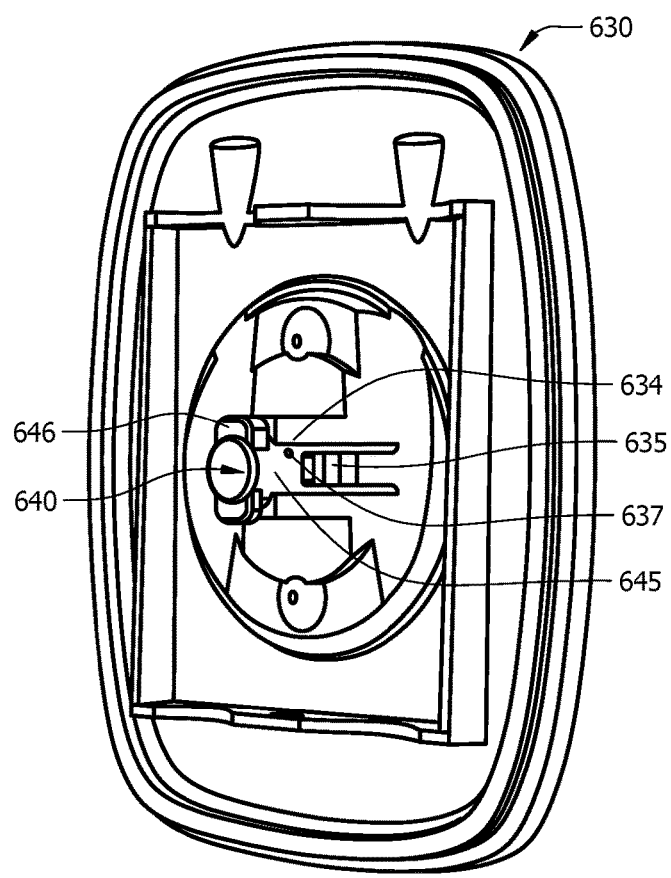
FIG. 6B illustrates a back/interior view of an exemplary embodiment of a removable cover comprising a key in the unlocked configuration and biased outward away from the removable cover, similar to the embodiment shown in FIG. 6A.

FIG. 6B illustrates a back/interior view of an exemplary embodiment of a removable cover 630 comprising a key 640 in the unlocked configuration and biased outward away from the removable cover 630, similar to the embodiment shown in FIG. 6A (showing the opposite/interior side of the removable cover 630 rather than the exterior side). In the exemplary embodiment of FIG. 6B, the elements (e.g. through-hole 637, pins 646, longitudinal member 645, etc.) are configured to interact similarly to the elements in the exemplary embodiment of FIG. 5B. In the embodiment of FIG. 6B, the interference elements are not visible as they are in the protruding member 634 (e.g. guide rail) of the removable cover 630. As the user pulls the key 640 outward away from the removable cover 630, the interference elements are configured to fit within the protruding member 634 to prevent rotation but allow inward and outward (e.g. linear) motion. Furthermore, the longitudinal member 645 may be able to move outward because the interference elements are not configured to interact with the flexible arms 635 in the unlocked configuration. If the key 640 was in the locked configuration, the user may not be able to move the key 640 outward (due to the fact that the interference elements would interact with the flexible arms 635 which would prevent further outward motion (the flexible arms 635 may be configured to allow inward motion but not outward motion)).

Figure 7A:
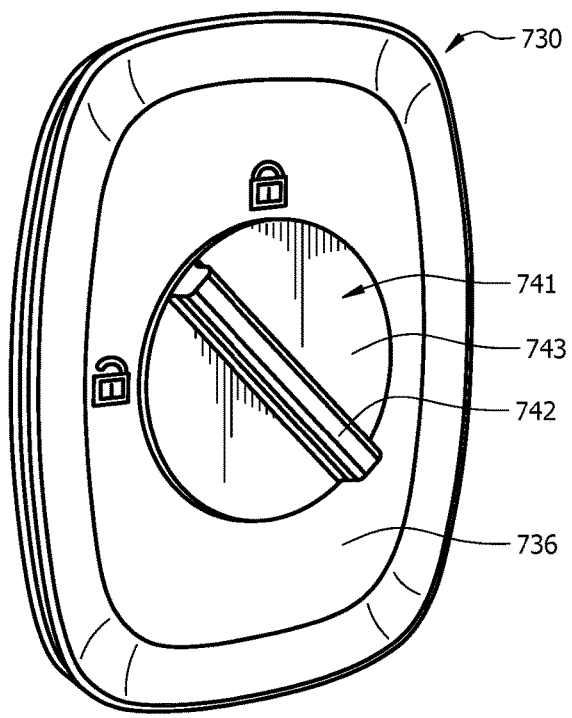
FIG. 7A illustrates a front view of an exemplary embodiment of a removable cover comprising a key in a partially locked configuration (e.g. neither locked nor unlocked)

FIG. 7A illustrates a front view of an exemplary embodiment of a removable cover 730 comprising a key in a partially locked configuration (e.g. neither entirely locked nor unlocked—e.g. mid turn as a user moves from the unlocked to the locked configuration or vice versa). The key is fully compressed/retract within the recessed portion of the main body panel portion of the removable cover, allowing turning of the raised grip. In the exemplary embodiment of FIG. 7A, the raised grip 742 of the grip surface 741 is configured to lay approximately half-way between the locked configuration and the unlocked configuration. The elements in the exemplary embodiment of FIG. 7A (e.g. grip surface 741, raised grip 742, circular back plate 743, main body panel portion 736, etc.) are similar to the elements shown in the exemplary embodiment of FIG. 5A and FIG. 6A. Thus, the elements in the exemplary embodiment of FIG. 7A function similarly to those in FIG. 5A and FIG. 6A.

Figure 7B:
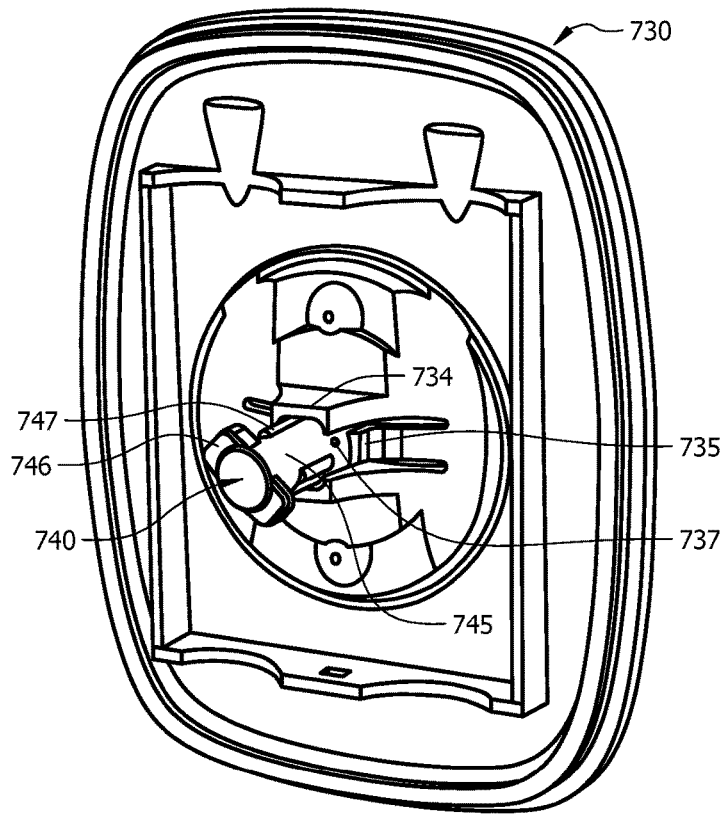
FIG. 7B illustrates a back/interior view of an exemplary embodiment of a removable cover comprising a key in the partially locked configuration (e.g. neither locked nor unlocked), similar to the embodiment shown in FIG. 7A.

FIG. 7B illustrates a back/interior view of an exemplary embodiment of a removable cover 730 comprising a key in the partially locked configuration (e.g. neither locked nor unlocked), similar to the embodiment shown in FIG. 7A (showing the opposite/interior side of the removable cover 730 rather than the exterior side). In the exemplary embodiment of FIG. 7B, the elements (e.g. interference elements 747, key 740, pin 746, longitudinal member 745, protruding member 734, flexible arms 735, through-hole 737, etc.) are configured to interact similarly to the elements in the exemplary embodiment of FIG. 5B and FIG. 6B. In the embodiment of FIG. 7B, the interference elements 747 are oriented diagonally (so that the interference elements 747 are not configured to fit within the protruding member 734 (e.g. guide rail) of the removable cover 730 or interact with the flexible arms 735 of the removable cover 730). In other words, in a partially locked/unlocked configuration, the key 740 may not be operable to move outward (from the through-hole 737) (e.g. away) from the removable cover 730 unless the user rotates the key 740 further so that the interference elements 747 align with the protruding member 734 and/or do not interact with the flexible arms 735.

Figure 8:
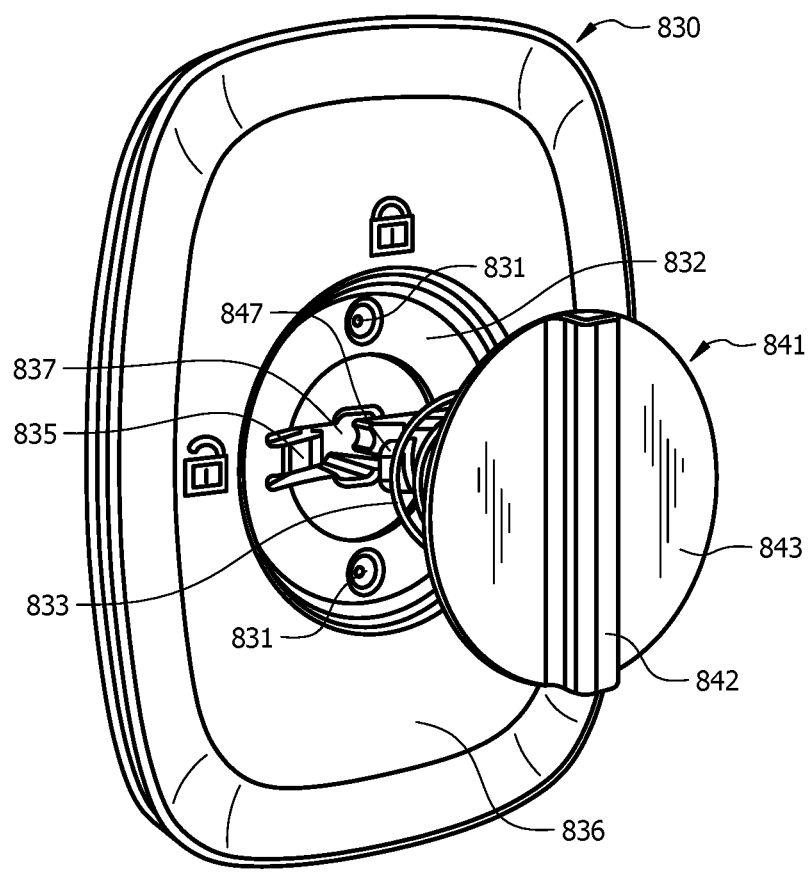
FIG. 8 illustrates a perspective view of an exemplary embodiment of a removable cover comprising a recessed portion, flexible arms, two cavities, and a key biased outward, via a bias element, away from the removable cover.

FIG. 8 illustrates an exploded perspective view of an exemplary embodiment of a removable cover 830 comprising a recessed portion 832, flexible arms 835, two cavities 831, and a key biased outward, via a bias element 833, away from the removable cover 830. In the exemplary embodiment shown in FIG. 8, the key is oriented in the locked configuration (e.g. the raised grip 842 oriented approximately vertically). Additionally, the key comprises a bias element 833 which is a spring in the embodiment of FIG. 8. The spring is configured to wrap around the longitudinal member. Additionally, the recessed portion 832 of the removable cover 830 comprises two cavities 831. The cavities 831 are configured to interact with the corresponding number of protrusions located on the backside of the grip surface 841 (e.g. circular back plate 843) of the key (e.g. to establish a barrier/resistance to overcome when configuring the device to/towards the unlocked configuration) (e.g. the device further comprising a resistance mechanism configured to provide a pre-set amount of resistance with respect to (rotation of the key to) moving from locked to unlocked configuration). Additionally, the key is configured to fit through the through-hole 837 of the removable cover 830. Thus, once the user inserts the key into the through-hole 837 and pushes/depresses inward, the interference elements 847 may interact with the flexible arms 835 to push the flexible arms 835 inward to create room for the key to enter via the through-hole 837. In this manner, the flexible arms 835 provide an extra resistance to overcome (in addition to the cavities 831 and the bias element 833) when attempting to lock the removable cover 830 using the key. Generally, once the key is in the locked configuration, it is configured to fit snugly within the recessed portion 832 of the removable cover 830 (the circular back plate 843 of the key lying flush with the main body panel portion 836 of the removable cover 830). In some embodiments, the raised grip 842 may extend outward in comparison to the main body panel portion 836 to allow the user to more easily find/grasp the key.

Having described device and method embodiments above, especially with regard to the figures, various additional embodiments can include, but are not limited to the following:

In a first embodiment, a hearing protection device comprising: at least one ear cup (each having a sealing element, e.g. configured to seal a user's ear canal, for example to provide a Noise Reduction Rating (NRR) of 20 or greater); and a battery compartment; wherein: the battery compartment is incorporated within the ear cup (e.g. so that the battery compartment is mounted within the ear cup and is encompassed entirely by the ear cup); the battery compartment further comprises a removable cover (oriented/located on an outer surface of the ear cup, e.g. the removable cover forms a portion of the outer surface of the ear cup) (and a recessed body configured to receive batteries); the removable cover comprises a key and a main body panel portion; (the key is configured to be attached to the main body panel portion in a manner allowing the key to slide longitudinally with respect to the main body panel portion (while remaining (permanently) attached at all times (e.g. because the distal end of the key (and the raised grip) is larger than the hole/opening in the main body panel portion through which the longitudinal member of the key passes (e.g. through-hole)));) the removable cover further comprises a bias element configured to bias the key outward (e.g. allowing the key to automatically project outward away from the main body panel portion of the removable cover in the unlocked configuration); the battery compartment further comprises a (lock-fit/corresponding) aperture; the key further comprises a grip surface (which might for example comprise a (central) raised grip) (on the outer surface) and a longitudinal member (configured to extend inward (from the grip surface) into the battery compartment when the removable cover is attached/locked in place on the battery compartment) having a distal end shaped to interact/correspond with the (lock-fit/corresponding) aperture to provide two configurations (for the removable cover); (the lock-fit/corresponding aperture is located on the innermost portion (e.g. back-wall) of the battery compartment (e.g. behind the batteries) and/or between the battery locations—so that the longitudinal member of the key may extend between the batteries in operation when the cover is locked in place and the batteries are in the battery compartment;) and the two configurations comprise a locked configuration (e.g. with the distal end of the key oriented so that it is securely (longitudinally) locked/fixed within the aperture (e.g. preventing longitudinal movement of the key with respect to the battery compartment/aperture (although allowing rotational movement)), such that the removable cover is securely and/or sealingly attached to the battery compartment in a fixed manner) and an unlocked configuration (e.g. with the distal end of the key oriented to allow free longitudinal movement of the key with respect to the battery compartment/aperture, such that the removable cover is free to be removed from the battery compartment, e.g. removable so as to allow access to the inside of the battery compartment for a battery change). A second embodiment can include the hearing protection device of the first embodiment, wherein the grip surface comprises a (central) raised grip which extends/projects outward away from the hearing protection device (e.g. outward from the outer surface of the ear cup and/or outward/away from the user's ears when the user is wearing the hearing protection device). A third embodiment can include the hearing protection device of the first or second embodiments, wherein the (central) raised grip is configured for ease of use by a user's gloved hand (e.g. for interaction with a user's hands (e.g. with the user's gloved hands) (e.g. the user's fingers gripping the (central) raised grip to switch between the two configurations)). A fourth embodiment can include the hearing protection device of the first to third embodiments, wherein the grip surface on the key further comprises a circular back plate (and a raised grip) (configured to provide a larger grip surface area (e.g. larger than merely the raised grip) for the (exterior face of the) key, to facilitate removal of the removable cover from the battery compartment with a gloved hand)(e.g. the circular back plate may be approximately 20-35 millimeters), wherein the raised grip is mounted on the exterior of the circular back plate (e.g. the circular back plate interfaces with the (central) raised grip), and wherein the circular back plate is configured to interface/interact with the removable cover (e.g. the circular back plate is larger than the opening in the main body panel portion of the removable cover, and is configured to allow rotation of the key/circular back plate/raised grip with respect to the main body panel portion of the removable cover). A fifth embodiment can include the hearing protection device of the first to fourth embodiments, wherein the (front/exterior/outer portion/surface of the) main body panel portion of the removable cover further comprises a recessed portion, wherein the recessed portion corresponds with the (grip surface, e.g. raised grip and/or circular back plate of the) key (e.g. such that the circular back plate and/or raised grip fits within the recessed portion), and (wherein the grip surface, e.g. circular back plate of the key is configured to fit snugly within the recessed portion (e.g. substantially fill the recessed portion and/or be shaped similarly/correspondingly, so as to allow rotation of the key without any interference by the recessed portion). A sixth embodiment can include the hearing protection device of the first to fifth embodiments, wherein in the locked configuration, the (central) raised grip of the key is configured to lay flush with the outer surface of the removable cover. A seventh embodiment can include the hearing protection device of the first to sixth embodiments, wherein in the locked configuration, the grip surface is configured to lie at least partially within the recessed portion of the battery compartment (e.g. the circular back plate is configured to lie entirely within the recessed portion so as to be flush with the outer surface of the removable cover, while the raised grip projects out from the recessed portion, or the circular back plate is configured to lie entirely within the recessed portion (but perhaps be a bit indented from the outer surface) and the raised grip projects out from the recessed portion). An eighth embodiment can include the hearing protection device of the first to seventh embodiments, wherein in the unlocked configuration, the key (pops out automatically and) is biased outward away from the (outer/exterior) surface of the removable cover (e.g. a biasing element is configured with respect to the key so that, in the unlocked position, the key automatically pops outward with respect to the main body panel portion of the removable cover) (e.g. the key pops out approximately 5-10 millimeters). A ninth embodiment can include the hearing protection device of the first to eighth embodiments, wherein to switch between the locked configuration and the unlocked configuration, the (central) raised grip undergoes a 90 degree turn/rotation (e.g. anticlockwise). A tenth embodiment can include the hearing protection device of the first to ninth embodiments, wherein the bias element is a spring. An eleventh embodiment can include the hearing protection device of the first to tenth embodiments, wherein the bias element is located between and interfaces with the grip surface of the key and the exterior/outer surface/recessed portion of the removable cover (e.g. typically the biasing element is located in the recessed portion of the main body panel of the removable cover, between and contacting the grip surface of the key and the exterior of the main body panel portion of the removable cover) (e.g. there is no outward biasing element with respect to the main body portion of the removable cover, such that the main body panel portion of the removable cover is not biased outward with respect to the recessed body of the battery cover—rather only the key of the removable cover is typically biased outward). A twelfth embodiment can include the hearing protection device of the first to eleventh embodiments, wherein the bias element is located within the lock-fit aperture (which is located at the back of the battery compartment (e.g. back of battery compartment between the batteries)). A thirteenth embodiment can include the hearing protection device of the first to twelfth embodiments, wherein the battery compartment is welded (e.g. via ultrasonic welding) in place within the ear cup (shell) to prevent communication of air between the battery compartment and the inside of the ear cup (and to maintain sound attenuation of the hearing protection device). A fourteenth embodiment can include the hearing protection device of the first to thirteenth embodiments, wherein a first sealing element is located (e.g. around the circumference/lip/interface) between the removable cover and the ear cup and/or a second sealing element is located between the grip surface of the key and the main body portion of the removable cover (e.g. to prevent water and/or air from entering the hearing protection device (e.g. International Protection (IP) rating of IP54; IP54 is a classification designated to devices which prevent water from being sprayed into the device from any direction) (e.g. the first seal is located on either the outer edge circumference of the removable cover main body portion or on the circumference of the opening of the recessed body of the battery compartment (which interfaces with the circumference of the removable cover main body portion) and/or the second real is located on either the outer edge circumference of the grip surface of the key or on the circumference of the recessed portion of the main body portion of the removable cover (which interfaces with the circumference of the grip surface of the key). A fifteenth embodiment can include the hearing protection device of the first to fourteenth embodiments, further comprising a linking element (such as a rubber string), wherein the linking element connects the removable cover to the battery compartment (e.g. to ensure the removable cover remains attached to the hearing protection device even in the unlocked configuration; e.g. to prevent the removable cover from being lost), and wherein the linking element provides enough play/slack so that the removable cover can, in the unlocked configuration, be moved clear of the opening for the recessed body of the battery compartment (to allow access for changing of batteries)(e.g. length of linking element is 40-50 millimeters). A sixteenth embodiment can include the hearing protection device of the first to fifteenth embodiments, further comprising one or more protrusions and a corresponding number (and shape) of cavities, wherein the one or more protrusions are located on the backside/underside of the circular back plate of the key, wherein the corresponding number of cavities are located within the recessed portion of the main body panel portion of the removable cover, and wherein, in the locked configuration, the one or more protrusions are configured to align (e.g. fit within) with the corresponding number of cavities (to create a firm locked grip) (e.g. to establish a barrier/resistance to overcome when configuring the device to/towards the unlocked configuration) (e.g. the device further comprising a resistance mechanism configured to provide a pre-set amount of resistance with respect to (rotation of the key to) moving from locked to unlocked configuration. A seventeenth embodiment can include the hearing protection device of the first to sixteenth embodiments, wherein the main body portion of the removable cover further comprises a through-hole corresponding to the longitudinal member of the key, and wherein the longitudinal member of the key is configured to run through the through-hole of the removable cover, through the center of the battery compartment (e.g. between two batteries), and into the corresponding/lock-fit/lock-fit aperture (when in the locked configuration). An eighteenth embodiment can include the hearing protection device of the first to seventeenth embodiments, wherein the longitudinal member further comprises an interference element and a pin (e.g. the pin forms the distal end of the key), and wherein the (back-side/underside/inner surface of the) removable cover further comprises a protruding member (e.g. guide rail) configured for interaction with the interference element. A nineteenth embodiment can include the hearing protection device of the first to eighteenth embodiments, wherein in the unlocked configuration, when the key is biased outward away from the removable cover, the interference element is configured to fit within the protruding member allowing for longitudinal (e.g. inward and outward-forward and backward motion (e.g. linear motion) (e.g. not rotational motion)) of the key (e.g. the protruding member acts as (at least a partial) guide rail, allowing longitudinal movement of the pin (when the interference element interfaces with the protruding member) but preventing rotation of the key (when the interference element interfaces with the protruding member). A twentieth embodiment can include the hearing protection device of the first to nineteenth embodiments, wherein the key is biased outward away from the removable cover by at least 5 millimeters (to allow the user to use his/her fingers to grip the key to pull the removable cover off of the battery compartment). A twenty-first embodiment can include the hearing protection device of the first to twentieth embodiments, wherein the key is biased outward away from the removable cover until the pin interfaces with the protruding member (which restricts further outward (e.g. away from the battery compartment) motion of the key (and keeps the key (securely) attached to the removable cover in both the unlocked configuration and the locked configuration)). A twenty-second embodiment can include the hearing protection device of the first to twenty-first embodiments, wherein (maximum/full) depression of the bias element allows the pin to fit within the (lock-fit/corresponding/lock-fit) aperture of the battery compartment, wherein (maximum/full) depression of the bias element allows for rotation of the key (from locked to unlocked configuration), and wherein, when rotated to the locked configuration, the pin is configured to lock into the lock-fit aperture (so that without further rotation, the key will not be move longitudinally). A twenty-third embodiment can include the hearing protection device of the first to twenty-second embodiments, wherein the removable cover further comprises two or more flexible arms, wherein (in the locked configuration) the two or more flexible arms are configured to contract/flex inward to allow the key to push through the aperture of the removable cover and fit into the lock-fit aperture of the battery compartment, and wherein the two or more flexible arms prevent outward motion of the key (preventing the key from unlocking while in the locked configuration)(preventing the key from falling off/separating from the removable cover (for example, when the removable cover is detached from the ear cup).

Exemplary embodiments might also relate to methods for using a hearing protection device comprising a removable cover operable to be unlocked and locked using a key (e.g. similar to those described above, which may be considered optionally incorporated herein with respect to the discussion of the methods). Such method embodiments, for example, might include, but are not limited to, the following:

In a twenty-fourth embodiment, a method for configuring (e.g. removing and attaching, such as unlocking and locking) a removable cover from a battery compartment of a hearing protection device using a key and/or a method for replacing batteries of a hearing protection device using a removable cover comprising a key, the method comprising: rotating the key (90 degrees) (a first direction—e.g. anticlockwise)(using a grip surface of the key, typically using a raised grip of the grip portion); biasing outward, by a bias element, the key from the main body portion of the removable cover (e.g. not the entire removable cover); pulling the key (all the way out) to remove the removable cover from a battery compartment (with the distal end of the key interfacing with the main body panel portion of the removable cover)(maintaining the key within the main body panel portion of the removable cover even in the unlocked configuration)(e.g. using a circular back plate of the grip portion of the key to provide a larger grip surface); (the cover being held in proximity to the battery compartment while it is uncoupled (e.g. by a linking element)); (replacing the batteries—e.g. removing old batteries and/or inserting new batteries); (using the entire grip surface (e.g. circular back plate) to position the removable cover main body portion in (sealing) place atop the recessed body of the battery compartment); depressing the key until fully depressed; and rotating the key (the opposite direction—e.g. 90 degrees (clockwise)) (e.g. using the raised grip) until the key is locked into a lock-fit aperture within the battery compartment. A twenty-fifth embodiment can include the method of the twenty-fourth embodiment, wherein the bias element comprises a spring. A twenty-sixth embodiment can include the method of the twenty-fourth to twenty-fifth embodiments, wherein rotating the key further comprises turning the key using a raised grip located on the outward side of the key and located within a recessed portion of the removable cover. A twenty-seventh embodiment can include the method of the twenty-fourth to twenty-sixth embodiments, wherein the key further comprises a circular back plate and wherein biasing outward of the key from the removable cover creates a larger surface area (e.g. the entire circular back plate) to allow the user to use his/her hands to grasp the key to pull the removable cover from the battery compartment (to remove the cover). A twenty-eighth embodiment can include the method of the twenty-fourth to twenty-seventh embodiments, wherein the main body portion of the removable cover is not biased outward (e.g. away from the recessed body of the battery compartment), but only the key is biased outward with respect to the main body portion of the removable cover. A twenty-ninth embodiment can include the method of the twenty-fourth to twenty-eighth embodiments, wherein the battery compartment is sealingly attached (e.g. by ultrasonic welding) to the ear cup (so that no air and/or water communication) (to prevent/minimize reduction in NRR level of ear cup).

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A hearing protection device comprising:
   at least one ear cup;
   a battery compartment incorporated within the ear cup; and
   a removable cover comprising a main body panel portion and a key disposed within the main body panel portion, the key comprising a grip surface, a longitudinal member, and a pin disposed at a distal end of the longitudinal member, the key being rotatable between a locked configuration and an unlocked configuration,
   wherein the battery compartment comprises a lock-fit aperture and a bias element configured to bias the key outward, and
   wherein the pin disposed at a distal end of the longitudinal member is configured to interact with the lock-fit aperture.

2. The hearing protection device of claim 1 wherein the grip surface comprises a raised grip which projects outward away from the hearing protection device.

3. The hearing protection device of claim 2 wherein the raised grip is configured for ease of use by a user's gloved hand, and wherein to switch between the locked configuration and the unlocked configuration, the raised grip is configured to undergo a rotation.

4. The hearing protection device of claim 2 wherein, in the locked configuration, the raised grip of the key is configured to lay flush with the outer surface of the removable cover.

5. The hearing protection device of claim 2 wherein the grip surface on the key further comprises a circular back plate, wherein the raised grip is mounted on the exterior of the circular back plate, and wherein the circular back plate is configured to interact with the removable cover.

6. The hearing protection device of claim 5 further comprising one or more protrusions and a corresponding number of cavities, wherein the one or more protrusions are located on the backside/underside of the circular back plate of the key, wherein the corresponding number of cavities are located within the recessed portion of the main body panel portion of the removable cover, and wherein, in the locked configuration, the one or more protrusions are configured to align with the corresponding number of cavities.

7. The hearing protection device of claim 6 wherein the longitudinal member of the key is configured to run through the through-hole of the removable cover, through the center of the battery compartment, and into the lock-fit aperture.

8. The hearing protection device of claim 5 wherein the recessed portion of the removable cover further comprises a through-hole corresponding to the longitudinal member of the key.

9. The hearing protection device of claim 1 wherein the main body panel portion of the removable cover further comprises a recessed portion, wherein the recessed portion corresponds with the key.

10. The hearing protection device of claim 9 wherein, in the locked configuration, the grip surface is configured to lie at least partially within the recessed portion of the removable cover.

11. The hearing protection device of claim 10 wherein in the unlocked configuration, when the key is biased outward away from the removable cover, the interference element is configured to fit within the protruding member allowing for longitudinal motion of the key.

12. The hearing protection device of claim 1 wherein, in the unlocked configuration, the key is biased outward away from the surface of the removable cover.

13. The hearing protection device of claim 1 wherein the bias element is a spring.

14. The hearing protection device of claim 1 wherein the bias element is located between and interfaces with the grip surface of the key and an exterior portion of the removable cover.

15. The hearing protection device of claim 1 wherein the bias element is located within the lock-fit aperture.

16. The hearing protection device of claim 1 wherein the battery compartment is welded in place within the ear cup to prevent communication of air between the battery compartment and the inside of the ear cup.

17. The hearing protection device of claim 16 wherein the longitudinal member further comprises an interference element and a pin, and wherein the removable cover further comprises a protruding member configured for interaction with the interference element.

18. The hearing protection device of claim 1 wherein a first sealing element is located between the removable cover and the ear cup and a second sealing element is located between the grip surface of the key and the main body panel portion of the removable cover.

19. The hearing protection device of claim 1 further comprising a linking mechanism, wherein the linking mechanism connects the removable cover to the battery compartment, and wherein the linking mechanism provides enough play/slack so that the removable cover can, in the unlocked configuration, be moved clear of the opening for the recessed body of the battery compartment.

20. The hearing protection device of claim 1 wherein depression of the bias element allows the pin to fit within the lock-fit aperture of the battery compartment, wherein depression of the bias element allows for rotation of the key, and wherein, when rotated to the locked configuration, the pin is configured to lock into the lock-fit aperture.

* * * * *